US012053388B2

(12) United States Patent
Zhu et al.

(10) Patent No.: US 12,053,388 B2
(45) Date of Patent: Aug. 6, 2024

(54) TIBIAL SUPPORT OF ARTIFICIAL KNEE JOINT

(71) Applicant: Jiangsu Okani Medical Technology Co., Ltd., Taicang (CN)

(72) Inventors: Jack Zhu, Taicang (CN); Longwei Xu, Taicang (CN)

(73) Assignee: Jiangsu Okani Medical Technology Co., Ltd., Taicang (CN)

( * ) Notice: Subject to any disclaimer, the term of this patent is extended or adjusted under 35 U.S.C. 154(b) by 60 days.

(21) Appl. No.: 17/581,278

(22) Filed: Jan. 21, 2022

(65) Prior Publication Data

US 2022/0142786 A1 May 12, 2022

Related U.S. Application Data

(63) Continuation of application No. 15/572,325, filed as application No. PCT/CN2015/000726 on Oct. 28, 2015, now abandoned.

(30) Foreign Application Priority Data

May 8, 2015 (CN) .......................... 201510232801.5

(51) Int. Cl.
*A61F 2/38* (2006.01)
*A61F 2/30* (2006.01)
*A61F 2/34* (2006.01)

(52) U.S. Cl.
CPC ................ *A61F 2/389* (2013.01); *A61F 2/38* (2013.01); *A61F 2/3886* (2013.01);
(Continued)

(58) Field of Classification Search
None
See application file for complete search history.

(56) References Cited

U.S. PATENT DOCUMENTS 4,808,185 A * 2/1989 Penenberg ......... A61B 17/1624
623/20.29
4,944,757 A * 7/1990 Martinez ................. A61F 2/389
623/20.15
(Continued)

FOREIGN PATENT DOCUMENTS

CN 102058446 A 5/2011
CN 202920327 U 5/2013
(Continued)

OTHER PUBLICATIONS

English Translation of International Search Report from International Patent Application No. PCT/CN2015/000726, dated Feb. 18, 2016, 6 pages.
(Continued)

*Primary Examiner* — Ann Schillinger
(74) *Attorney, Agent, or Firm* — Westman, Champlin & Koehler, P.A.

(57) ABSTRACT

A tibial support of an artificial knee joint, comprising a main tibial support body (100) and a tibial support platform (200), wherein the main tibial support body (100) is wing-shaped, a central axis thereof being vertical to the tibial support platform (200). A plurality of hollow screw holes is provided at the upper part of the main body (100). The tibial support platform (200) is located above the main tibial support body (100). The surface of the tibial support platform (200) is an organic polymer material layer matching a tibial liner. The hollow screw holes in the tibial support are sealed by the polymer material layer. Because a tibial support of an artificial knee joint adopts a high-biocompatibility organic polymer material, physical machining is allowed in an operation, and meanwhile, the surface corrosion of the tibial support is reduced. Hollow screw holes are sealed by means of a polymer material layer, thereby inhibiting joint liquid from entering the holes, and reducing the transportation of
(Continued)

particles. Recesses (201) are provided at positions, corresponding to the screw holes, on the polymer surface, thereby aiding in drilling holes and mounting screws in an operation.

19 Claims, 2 Drawing Sheets

(52) U.S. Cl.
    CPC ............... *A61F 2002/3006* (2013.01); *A61F 2002/30433* (2013.01); *A61F 2002/30604* (2013.01); *A61F 2002/30884* (2013.01); *A61F 2220/0025* (2013.01)

(56) References Cited

U.S. PATENT DOCUMENTS

| | | | | |
|---|---|---|---|---|
| 5,171,276 A | * | 12/1992 | Caspari | A61F 2/38 606/92 |
| 5,413,605 A | * | 5/1995 | Ashby | A61F 2/30771 623/20.34 |
| 5,571,198 A | | 11/1996 | Drucker et al. | |
| 5,609,642 A | * | 3/1997 | Johnson | A61F 2/461 606/88 |
| 5,658,341 A | * | 8/1997 | Delfosse | A61F 2/38 623/20.32 |
| 5,824,103 A | * | 10/1998 | Williams | A61F 2/389 623/20.32 |
| 5,876,456 A | * | 3/1999 | Sederholm | A61F 2/34 623/16.11 |
| 5,911,758 A | * | 6/1999 | Oehy | A61F 2/30744 623/20.32 |
| 6,120,546 A | * | 9/2000 | Dye | A61F 2/34 623/18.11 |
| 8,715,359 B2 | * | 5/2014 | Deffenbaugh | A61F 2/4202 623/20.14 |
| 8,998,997 B2 | * | 4/2015 | Ries | A61F 2/3868 623/20.27 |
| 9,204,969 B2 | * | 12/2015 | Thomas | A61F 2/389 |
| 9,237,953 B2 | * | 1/2016 | Rybolt | A61F 2/38 |
| 9,597,189 B2 | * | 3/2017 | Katerberg | A61F 2/389 |
| 9,675,464 B2 | * | 6/2017 | Jerry | A61F 2/389 |
| 9,744,044 B2 | * | 8/2017 | Cohen | A61F 2/38 |
| 2003/0014122 A1 | * | 1/2003 | Whiteside | A61F 2/389 623/20.32 |
| 2005/0055101 A1 | * | 3/2005 | Sifneos | A61F 2/389 623/22.13 |
| 2008/0114463 A1 | * | 5/2008 | Auger | A61F 2/3868 623/20.33 |
| 2010/0100190 A1 | * | 4/2010 | May | A61F 2/38 623/20.14 |
| 2010/0331737 A1 | * | 12/2010 | Stein | A61B 5/6878 600/587 |
| 2011/0295377 A1 | * | 12/2011 | Dees, Jr. | A61F 2/3868 623/20.32 |
| 2013/0006371 A1 | * | 1/2013 | Wogoman | A61F 2/461 623/20.21 |
| 2014/0284016 A1 | * | 9/2014 | Vander Wal | B22C 7/02 164/245 |
| 2018/0049878 A1 | * | 2/2018 | Stulberg | A61F 2/389 |

FOREIGN PATENT DOCUMENTS

| | | | |
|---|---|---|---|
| CN | 104887355 A | 9/2015 | |
| CN | 204709087 U | 10/2015 | |
| EP | 0645126 A2 | 3/1995 | |
| JP | 2006175210 A | * 7/2006 | ............. A61F 2/389 |

OTHER PUBLICATIONS

Ahmad et al. "Arthroplasty—Current Strategies for the Management of Knee Osteoarthritis", Journal of the Swiss Society of Infectious Diseases, the Swiss Society Internal Medicine, the Swiss Society of Pneumology, dated Feb. 9, 2015, 17 pages.

Lee et al. "Effects of Screw Types in Cementless Fixation of Tibial Tray Implants: Stability and Strength Assessment", Clinical Biomechanics 14, 258-264, dated May 14, 1999, 7 pages.

Walter et al. "Mechanisms for Pumping Fluid Through Cementless Acetabular Components with Holes", The Journal of Arthoplasty vol. 20 No. 8, dated Dec. 8, 2005, 7 pages.

* cited by examiner

TIBIAL SUPPORT OF ARTIFICIAL KNEE JOINT

CROSS-REFERENCE TO RELATED APPLICATION(S)

This Application is a continuation of U.S. application Ser. No. 15/572,325, filed on Nov. 7, 2017, which published as U.S. Publication No. 2018/0125665, on May 10, 2018, which is a Section 371 National Stage Application of International Application No. PCT/CN2015/000726 filed Oct. 28, 2015 and published as WO 2016/179729 A1 on Nov. 17, 2016, and claims priority from Chinese Patent Application No. 201510232801.5, filed on May 8, 2015 before the Chinese Patent Office, the contents of which are hereby incorporated by reference in their entireties.

TECHNICAL FIELD

The present disclosure relates to a medical rehabilitation appliance, and more particularly to a tibial support of an artificial knee joint.

BACKGROUND

A tibial support of an artificial knee joint is widely used in total knee arthroplasty (Ahmad S S, Gantenbein B, Evangelopoulos D S, Schär MO, Schwienbacher S, Kohlhof H, Kohl S. Arthroplasty—current strategies for the management of knee osteoarthritis. Swiss Med Wkly. 2015 Feb. 9; 145:w14096. doi: 10.4414/smw.2015.14096. eCollection 2015.). However, in the case of the osteotomy being not accurate, especially in the case of non-cemented fixation, it needs to selectively use bone screws to fix, which can increase the initial stability of the prosthesis, and thus promote human bone into the prosthesis (Lee T Q, Barnett S L, Kim W C. Effects of screw types in cementless fixation of tibial tray implants: stability and strength assessment. Clin Biomech (Bristol, Avon). 1999 May; 14(4):258-64.). A traditional tibial support of the artificial knee joint is provided with vacant screw holes, which is used with bone screws in application. But the vacant screw holes facilitate the delivery of synovial fluid with microparticles to the bone prosthesis interface, and thus cause osteolysis, which has been well proven on the hip (Walter W L, Clabeaux J, Wright T M, Walsh W, Walter W K, Sculco T P. Mechanisms for pumping fluid through cementless acetabular components with holes. J Arthroplasty. 2005 December; 20(8): 1042-8).

Although there are already patents about using sealed plugs or openable metal films to achieve sealed vacant screws at present, it has serious defects that it is not easy to open and is easy to produce metal debris and others. Therefore, it still needs to explore how to solve the problems caused by the vacant screw holes in the tibial support of the artificial knee joint.

SUMMARY

In order to solve the above-mentioned problems and defects, the object of the present disclosure is to provide a tibial support of an artificial knee joint. The tibial support can effectively prevent the problems concerning joint fluid delivery caused by the vacant screw holes.

In order to achieve the above object, the present disclosure employs the following technical solutions:

A tibial support of an artificial knee joint, comprising a tibial support body and a tibial support platform, wherein:
the tibial support body is wing-shaped, wherein a central axis thereof is perpendicular to the tibial support platform, a plurality of hollow screw holes are provided at an upper part of the tibial support body;
the tibial support platform is located above the tibial support body, a surface of the tibial support platform is an organic polymer material layer that is cooperated with a tibial liner in shape, and the hollow screw holes in the tibial support are sealed by the polymer material layer.

Further, positions on an upper surface of the polymer material layer that correspond to the hollow screw holes have recesses.

Further, the polymer material is polyether-ether-ketone (PEEK) or derivatives thereof.

Further, the tibial support body is made of a metal material.

Further, the metallic material is selected from one of titanium, titanium alloy or CoCrMo.

Further, the tibial support body is made of a polymer organic material.

Further, the polymer organic material is polyether-ether-ketone or derivatives thereof.

Further, a microporous biocompatible metal layer is provided between the tibial support body and the tibial support platform.

Further, the microporous biocompatible metal layer is made of titanium or titanium alloy.

Further, the number of the hollow screw holes is greater than that of screws installed at the time of actual use.

Due to the employment of the above technical solutions, the present disclosure has the following advantages compared with the prior art:

Because the tibial support of the artificial knee joint of the present disclosure adopts an excellent-biocompatibility organic polymer material, physical machining is allowed in an operation, and meanwhile, the surface corrosion of the tibial support is reduced; the hollow screw holes are sealed by means of a polymer material layer, thereby inhibiting joint liquid from entering the holes, and reducing the delivery of particles; recesses are provided at positions of the polymer surface that correspond to the screw holes, thereby aiding in drilling holes and mounting screws in the operation.

LIST OF REFERENCE SIGNS

100 tibial support body, 200 tibial support platform, 201 recesses, 300 microporous biocompatible metal layer.

DETAILED DESCRIPTION

In order to make the objects, technical solutions and advantages of the present disclosure more clearly understood, the present disclosure will be described in further detail with reference to the accompanying drawings and embodiments below. It should be understood that the specific embodiments described herein are only used to explain the present disclosure and are not intended to limit the present disclosure.

Figure 1:
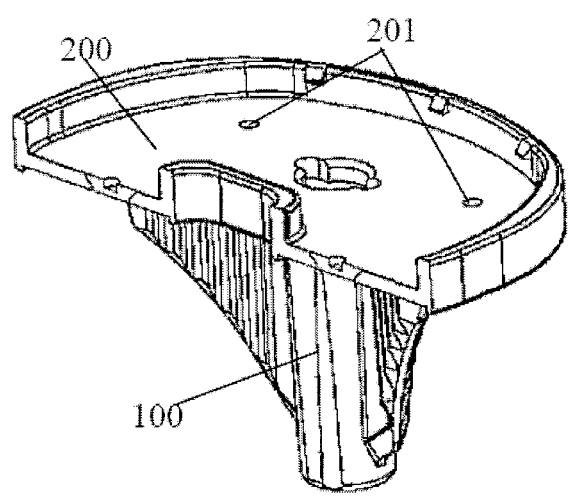
FIG. 1 is a schematic view of one embodiment of a tibial support of an artificial knee joint of the present disclosure.

As shown in FIG. 1, the tibial support of the artificial knee joint of the present disclosure comprises a tibial support body 100 and a tibial support platform 200, the tibial support body 100 is wing-shaped as a whole, wherein a central axis thereof is perpendicular to the tibial support platform 200, a plurality of hollow screw holes are provided at the upper part of the tibial support body 100, and the screw holes are cooperated with the bone screws during an operation, so that the stability of the prosthesis is reinforced, the tibial support platform 200 is located above the tibial support body 100, a surface shape of the tibial support platform 200 is cooperated with a tibial liner, a surface material of the tibial support platform 200 is an organic polymer material layer, the hollow screw holes in the tibial support body 100 are sealed by the polymer material layer. The polymer material layer can be reprocessed during the operation and can be cooperated with the bone screws after drilling. Positions on an upper surface of the polymer material layer that correspond to the hollow screw holes have recesses 201, and the recesses 201 are beneficial to selectively drill and position during the operation.

In a preferred embodiment, the polymeric material is an organic polymeric material having high strength and high stability, including, but not limited to, polyether-ether-ketone (PEEK), polyether-ether-ketone derivatives, polyether-ethers-ketone composite materials, ultrahigh molecular polyethylene, etc., the tibial support body 100 is made of a metallic material, which may be a biocompatible metallic material, including, but not limited to, titanium, titanium alloy, or CoCrMo and others.

Figure 2:
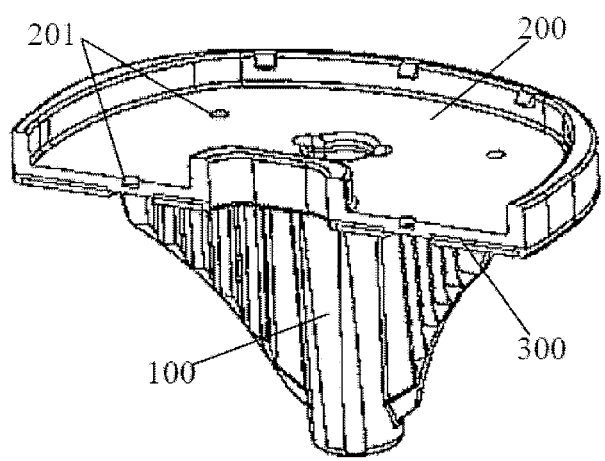
FIG. 2 is a schematic view of another embodiment of a tibial support of an artificial knee joint of the present disclosure.

In a preferred embodiment, as shown in FIG. 2, both the tibial support body 100 and the tibial support platform 200 are made of polyether-ether-ketone materials, and the tibial support body 100 and the tibial support platform 200 are also provided with a microporous biocompatible metal layer 300 on the surface that be in contact with the human bone, the material of the metal layer may be an excellent-biocompatibility material, such as titanium, titanium alloy or CoCrMo, etc. The microporous biocompatible metal layer 300 can promote bone ingrowth and achieve long term fixation.

In a preferred embodiment, the number of the hollow screw holes is greater than that of the bone screws required for practical use, and more screw holes can be provided to meet the needs of different types of cooperating parts. In use, it is only necessary to drill and install the recesses 201 where the bone screws are mounted, and the remaining screw holes are still sealed by the polymer material layer.

The above descriptions are only preferred embodiments of the present disclosure and are not intended to limit the implementation scope of the present disclosure; modifications or equivalent substitutions of the present disclosure should be covered in the protective scope of the claims of the present disclosure without departing from the spirit and scope of the disclosure.

The invention claimed is:

1. A tibial support of an artificial knee joint, comprising:
a tibial support body and a tibial support platform, wherein:
the tibial support body is wing-shaped, wherein a central axis thereof is perpendicular to the tibial support platform, and a plurality of hollow screw holes are provided at an upper part of the tibial support body; and
the tibial support platform is located entirely above the tibial support body, the tibial support platform comprising a single organic polymer material layer that is matched with a tibial liner in shape, wherein the plurality of hollow screw holes in the tibial support body are sealed by the single organic polymer material layer, and wherein a plurality of recesses are disposed on an upper surface of the single organic polymer material layer, each of the plurality of recesses positioned above one of the plurality of hollow screw holes.

2. The tibial support of the artificial knee joint as claimed in claim 1, characterized in that, the polymer material is polyether-ether-ketone or derivatives thereof.

3. The tibial support of the artificial knee joint as claimed in claim 2, characterized in that, the number of the hollow screw holes is greater than that of screws installed at the time of actual use.

4. The tibial support of the artificial knee joint as claimed in claim 2, characterized in that, the number of the hollow screw holes is greater than that of screws installed at the time of actual use.

5. The tibial support of the artificial knee joint as claimed in claim 1, characterized in that, the tibial support body is made of a metal material.

6. The tibial support of the artificial knee joint as claimed in claim 5, characterized in that, the metallic material is selected from one of titanium, titanium alloy or CoCrMo.

7. The tibial support of the artificial knee joint as claimed in claim 6, characterized in that, the number of the hollow screw holes is greater than that of screws installed at the time of actual use.

8. The tibial support of the artificial knee joint as claimed in claim 5, characterized in that, the number of the hollow screw holes is greater than that of screws installed at the time of actual use.

9. The tibial support of the artificial knee joint as claimed in claim 1, characterized in that, the tibial support body is made of a polymer organic material.

10. The tibial support of the artificial knee joint as claimed in claim 9, characterized in that, the polymer organic material is polyether-ether-ketone or derivatives thereof.

11. The tibial support of the artificial knee joint as claimed in claim 10, characterized in that, a microporous biocompatible metal layer is provided between the tibial support body and the tibial support platform.

12. The tibial support of the artificial knee joint as claimed in claim 11, characterized in that, the microporous biocompatible metal layer is made of titanium or titanium alloy.

13. The tibial support of the artificial knee joint as claimed in claim 9, characterized in that, the number of the hollow screw holes is greater than that of screws installed at the time of actual use.

14. The tibial support of the artificial knee joint as claimed in claim 10, characterized in that, the number of the hollow screw holes is greater than that of screws installed at the time of actual use.

15. The tibial support of the artificial knee joint as claimed in claim 11, characterized in that, the number of the hollow screw holes is greater than that of screws installed at the time of actual use.

16. The tibial support of the artificial knee joint as claimed in claim 12, characterized in that, the number of the hollow screw holes is greater than that of screws installed at the time of actual use.

17. The tibial support of the artificial knee joint as claimed in claim 1, characterized in that, the number of the hollow screw holes is greater than that of screws installed at the time of actual use.

18. A tibial support of an artificial knee joint, comprising:
a tibial support body and a tibial support platform, wherein:
the tibial support body is wing-shaped, wherein a central axis thereof is perpendicular to the tibial support platform, and a plurality of hollow screw holes are provided at an upper part of the tibial support body; and
the tibial support platform is located above the tibial support body, an upper surface of the tibial support platform is a single organic polymer material layer, the upper surface of the tibial support platform covering the plurality of hollow screw holes in the tibial support body, and wherein a plurality of recesses are disposed on the single organic polymer material layer, each of the plurality of recesses positioned above one of the plurality of hollow screw holes.

19. A tibial support of an artificial knee joint, comprising:
a tibial support body and a tibial support platform, wherein:
the tibial support body is wing-shaped, wherein a central axis thereof is perpendicular to the tibial support platform, and a plurality of hollow screw holes are provided at an upper part of the tibial support body; and
the tibial support platform is located above the tibial support body, a surface of the tibial support platform is a single organic polymer material layer that is matched in shape with a tibial liner that is positionable above the surface of the tibial support platform, and the surface of the tibial support platform seals the hollow screw holes in the tibial support body, and wherein a plurality of recesses are disposed on the single organic polymer material layer, each of the plurality of recesses positioned above one of the plurality of hollow screw holes.

* * * * *